United States Patent
Grumbles et al.

(10) Patent No.: US 9,261,392 B2
(45) Date of Patent: *Feb. 16, 2016

(54) FLUID-CONTROLLED ELECTRONIC GAMES AND MEASUREMENT DEVICES

(71) Applicant: Sharpshooter LLC, St. Paul, MN (US)

(72) Inventors: Ernest W. Grumbles, Saint Paul, MN (US); Timothy A. Bachman, Saint Paul, MN (US); John W. Ahern, Saint Paul, MN (US)

(73) Assignee: Sharpshooter LLC, St. Paul, MN (US)

( * ) Notice: Subject to any disclaimer, the term of this patent is extended or adjusted under 35 U.S.C. 154(b) by 238 days.

This patent is subject to a terminal disclaimer.

(21) Appl. No.: 14/041,547

(22) Filed: Sep. 30, 2013

(65) Prior Publication Data

US 2014/0190249 A1 Jul. 10, 2014

Related U.S. Application Data

(63) Continuation of application No. 13/418,825, filed on Mar. 13, 2012, now Pat. No. 8,544,341, which is a continuation-in-part of application No. 12/813,975, filed on Jun. 11, 2010, now abandoned.

(60) Provisional application No. 61/186,085, filed on Jun. 11, 2009, provisional application No. 61/552,807, filed on Oct. 28, 2011.

(51) Int. Cl.
| | | |
|---|---|---|
| G01F 1/00 | (2006.01) | |
| E03C 1/33 | (2006.01) | |
| A63F 9/00 | (2006.01) | |
| G01F 1/74 | (2006.01) | |
| E03D 13/00 | (2006.01) | |
| G01F 22/00 | (2006.01) | |
| G01F 1/075 | (2006.01) | |
| G01F 1/28 | (2006.01) | |
| G01F 15/06 | (2006.01) | |
| G01F 15/075 | (2006.01) | |
| A63F 9/24 | (2006.01) | |

(52) U.S. Cl.
CPC ... *G01F 1/74* (2013.01); *A63F 9/24* (2013.01); *E03D 13/005* (2013.01); *G01F 1/075* (2013.01); *G01F 1/28* (2013.01); *G01F 15/06* (2013.01); *G01F 15/075* (2013.01); *G01F 22/00* (2013.01)

(58) Field of Classification Search
None
See application file for complete search history.

(56) References Cited

U.S. PATENT DOCUMENTS

| | | |
|---|---|---|
| 5,078,012 A | 1/1992 | Ding et al. |
| 5,170,668 A | 12/1992 | Jones |
| 5,721,383 A | 2/1998 | Franklin et al. |
| 6,212,958 B1 | 4/2001 | Conley |
| 6,772,454 B1 | 8/2004 | Barry |
| 6,779,206 B1 | 8/2004 | Sykes |
| 6,856,934 B2 | 2/2005 | Vock et al. |

(Continued)

OTHER PUBLICATIONS

Whizometer™ Brand Urinometric Device, Owner's Manual, Twenty Acorns, Inc., copyright 2008, 3 pages.

(Continued)

*Primary Examiner* — Harshad R Patel
(74) *Attorney, Agent, or Firm* — Merchant & Gould P.C.

(57) ABSTRACT

A device for estimating a stream of urine entering a toilet or urinal includes a measuring unit configured to estimate an amount of the stream of urine, and an indicator to provide an indication to an individual of the amount of the stream of urine.

13 Claims, 14 Drawing Sheets

(56) References Cited

U.S. PATENT DOCUMENTS

| | | |
|---|---|---|
| 6,908,392 B2 | 6/2005 | Friedman |
| 6,971,272 B2 | 12/2005 | Förster et al. |
| 7,017,198 B2 | 3/2006 | Conn et al. |
| 7,194,776 B1 | 3/2007 | Lastuka et al. |
| 7,533,571 B2 | 5/2009 | Ariav et al. |
| 8,544,341 B2 | 10/2013 | Grumbles et al. |
| 2003/0035302 A1 | 2/2003 | Friedman |
| 2005/0038626 A1 | 2/2005 | Flentov et al. |
| 2005/0288105 A1 | 12/2005 | Piccionelli |
| 2006/0239645 A1 | 10/2006 | Curtner et al. |
| 2009/0095208 A1 | 4/2009 | Cardoza et al. |
| 2009/0165477 A1 | 7/2009 | Sturken et al. |
| 2010/0172205 A1 | 7/2010 | Hillesund et al. |
| 2010/0222932 A1 | 9/2010 | O'Connor |
| 2010/0313973 A1 | 12/2010 | Grumbles et al. |

OTHER PUBLICATIONS

Whizometer™ accessed at: www.twentyacorns.com, Jul. 1, 2009—update Apr. 26, 2010, 5 pages.

Winslett, Ryan, "Sega Toilet Games Make Public Restrooms More Fun," accessed at http://www.joystickdivision.com/2010/12/sega_toilet_games_make_public.php, posted Dec. 16, 2010, 4 pages.

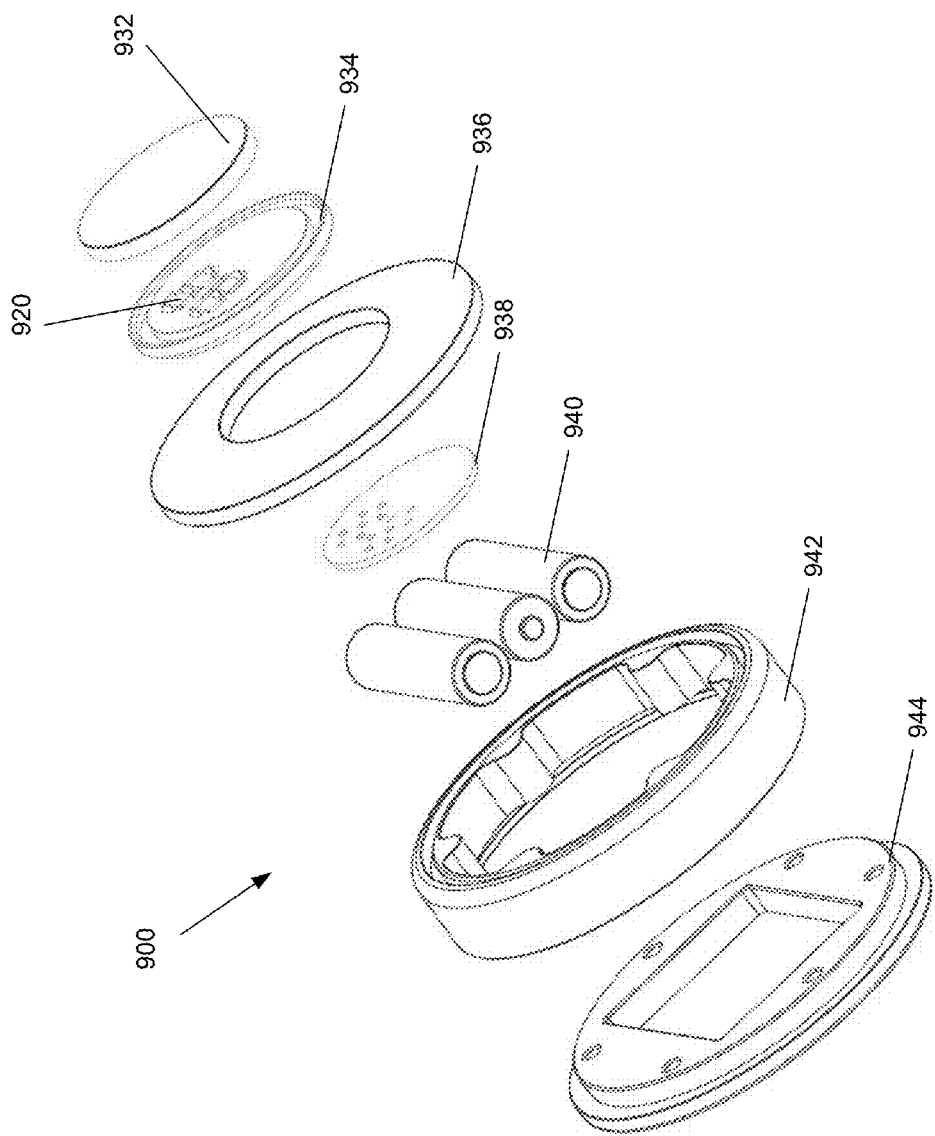

FLUID-CONTROLLED ELECTRONIC GAMES AND MEASUREMENT DEVICES

RELATED APPLICATIONS

This application is a continuation of U.S. Pat. No. 8,544,341, issued on Oct. 1, 2013, which is a continuation-in-part of U.S. patent application Ser. No. 12/813,975 filed on Jun. 11, 2010, which claims the benefit of U.S. patent application Ser. No. 61/186,085 filed on Jun. 11, 2009. U.S. Pat. No. 8,544,341 also claims the benefit of U.S. patent application Ser. No. 61/552,807 filed on Oct. 28, 2011. The disclosures of each of the above disclosed applications are hereby incorporated by reference in their entireties. To the extent appropriate, a claim of priority is made to each of the above disclosed applications.

BACKGROUND

Different games are used to entertain patrons at restaurants and bars, particularly during happy hour and "night life" activities. For example, many bars have karaoke nights to allow patrons to have fun as they socialize. Other popular bar activities include gambling and dancing. Entertainment has even made its way into the restrooms of the establishments. For example, many restrooms now are equipped with LCD panels that are positioned strategically around urinals and in stalls to entertain and advertise to patrons as they use the restroom facilities.

SUMMARY

In one aspect, a device for estimating a stream of urine entering a toilet or urinal includes a measuring unit configured to estimate an amount or time of the stream of urine, and an indicator to provide an indication to an individual of the amount or time of the stream of urine.

DESCRIPTION OF THE DRAWINGS

FIG. 14 is an exploded view of the flow mechanism of FIG. 12.

DETAILED DESCRIPTION

Examples described herein are directed to electronic games that can be provided in a restroom of a public establishment, such as a restaurant or bar. The games can be fluid-controlled, so that the games can be used to track or otherwise quantify an amount of urine that is produced by an individual or group of individuals. The games can be programmed to monitor and reward certain behaviors.

Figure 1:
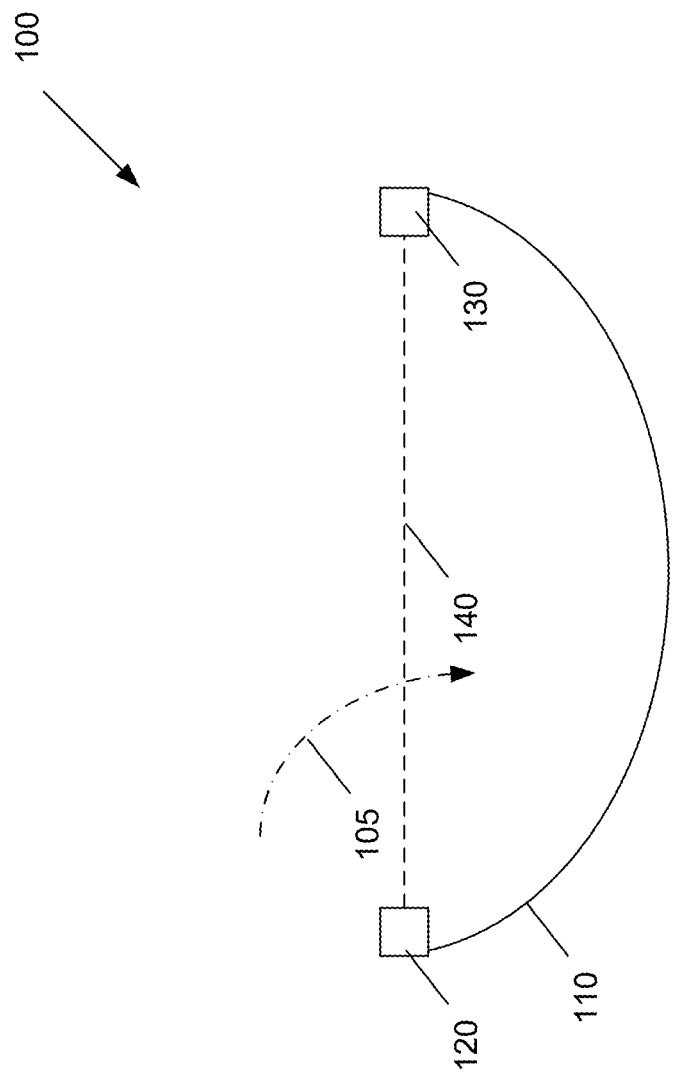
FIG. 1 shows an example system for estimating urine output.

Referring now to FIG. 1, one example system 100 is shown. The system 100 includes a standard toilet bowl 110 that is part of a typical toilet found in a public restroom. One or more sensors 120, 130 are affixed to the toilet bowl 110 so that the sensors 120, 130 create a beam 140 between the sensors. In the example shown, the sensors 120, 130 sense when the beam 140 is broken when an individual urinates into the toilet bowl 110.

For example, the urine stream 105 breaks the beam 140, and the sensors 120, 130 sense when the beam is broken. In this example, the sensors 120, 130 monitor a time for which the beam 140 is broken by the urine stream 105. This can be used, for example, to estimate an amount of urination for the individual. The sensors 120, 130 can be reset, for example, each time the toilet is flushed.

Figure 2:
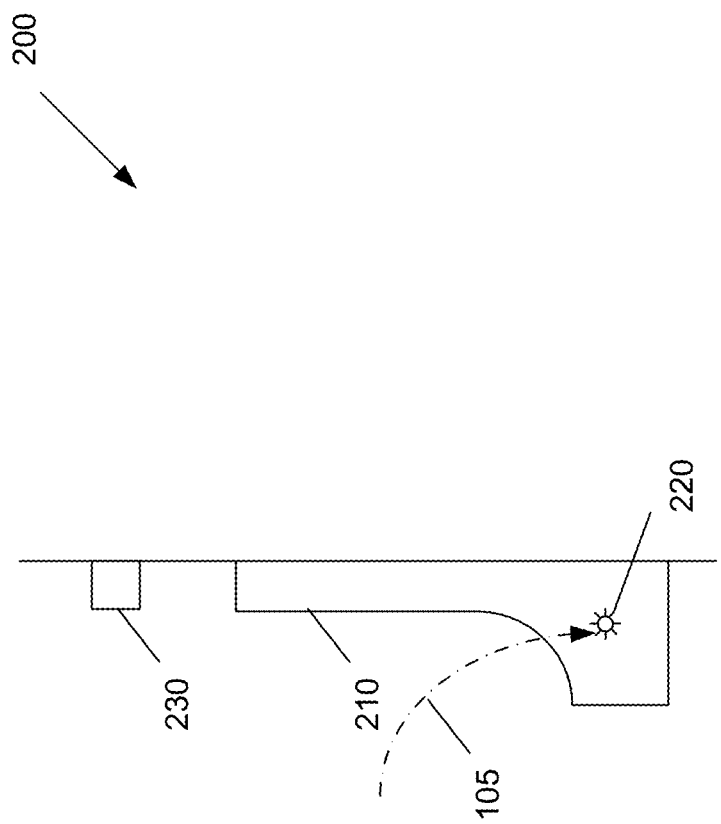
FIG. 2 shows another example system for estimating urine output.
Figure 3:
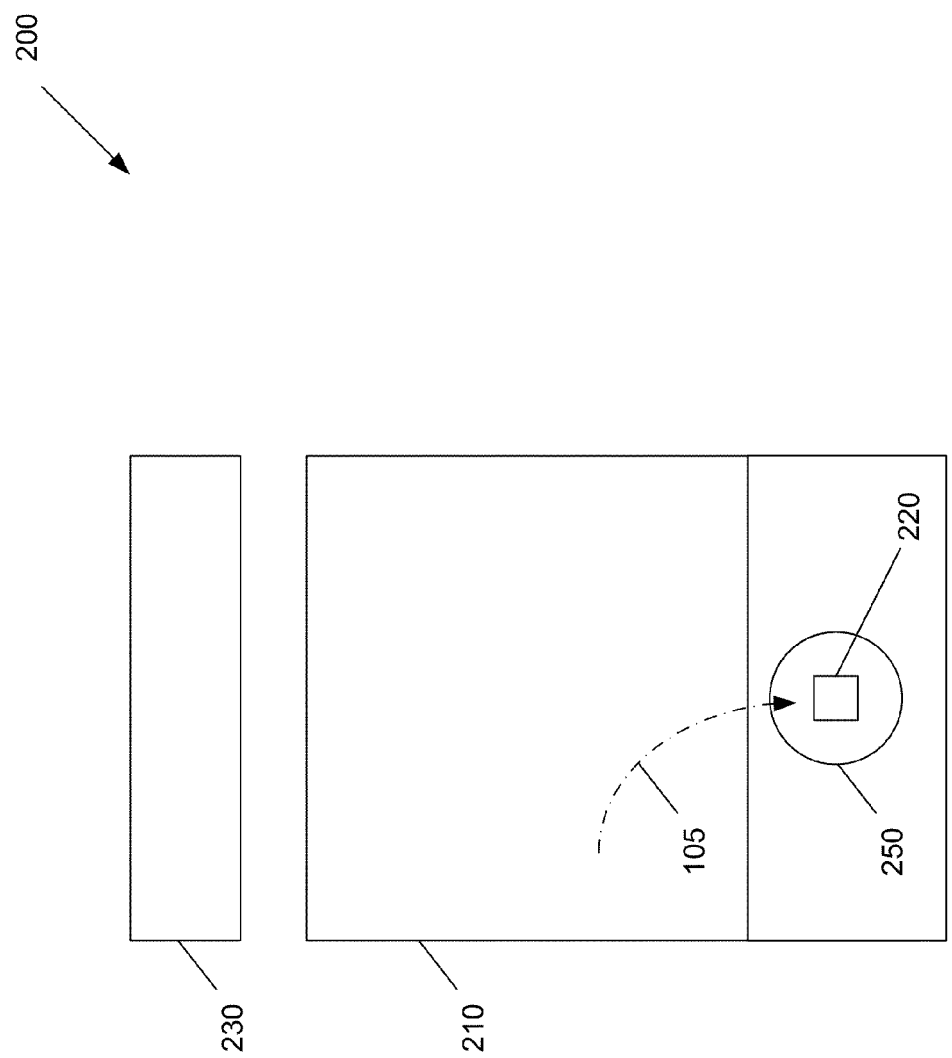
FIG. 3 shows another view of the system of FIG. 2.

Referring now to FIGS. 2 and 3, another example toilet system 200 is shown. The toilet system 200 includes a typical urinal 210. The urinal 210 includes a flow mechanism 220 that quantifies an amount of urination that is created by an individual. For example, in the embodiment shown, the flow mechanism 220 is a mechanical turbine that rotates as the urine stream 105 enters an aperture 250 formed in the urinal 210 and contacts and spins the flow mechanism 220. When the urine stream 105 stops, the flow mechanism 220 stops, and a controller connected to the flow mechanism 220 estimates a volume of urine based on the number of revolutions for the flow mechanism 220.

For example, the system 200 can include a digital module 230 that is connected through wired or wireless mechanisms to the flow mechanism 220. The digital module 230 can estimate an amount of urine and display the estimate to the individual, as described below.

Figure 4:
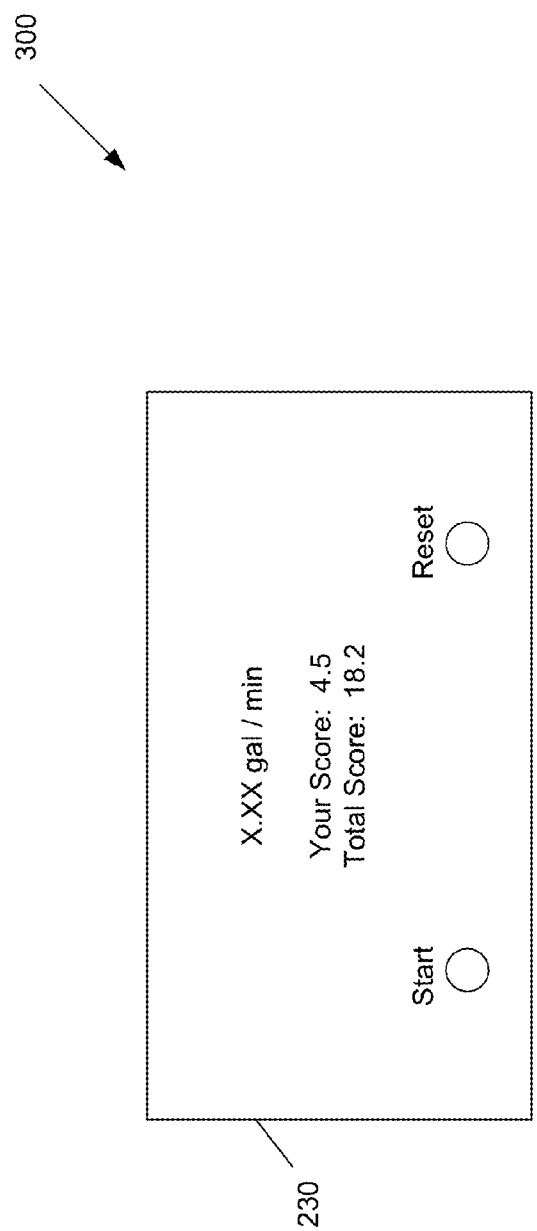
FIG. 4 shows an example user interface for a system for estimating urine output.

Referring now to FIG. 4, an example user interface 300. In the example shown, the user interface 300 is incorporated as part of the digital module 230. The user interface 300 includes a display, such as an LCD display, that displays information to the individual. This information can include the estimate of the urine production for the individual. Example information can include the estimate of production per quantity of time or rate (e.g., in gallons or liters per minute), actual production amount (e.g., in gallons or liters), actual fluid weight (e.g., in ounces or pounds), power generated through the urine stream, etc. Other information can also be displayed.

A score for the user can also be displayed, such as a total urine output score, or another score quantifying the individual's production as compared with others. In some examples, a total score can be produced that tracks an individual through multiple visits to the restroom. For example, the individual can provide a form of identification (e.g., a numeric identification number or simply the individual's name) so that the system 200 can track the individual's urine production over multiple trips to the restroom.

The interface 300 can also have interactive aspects, such as start and reset buttons. Other configurations are possible.

Various games can be associated with the systems 100, 200. For example, the bar or other establishment can create contests for the individual or individuals that generate the greatest amount of urine output in a particular time period. The contests can be based on individual output, or can be aggregated into groups. Other contest, as described below, can also be used.

Figure 5:
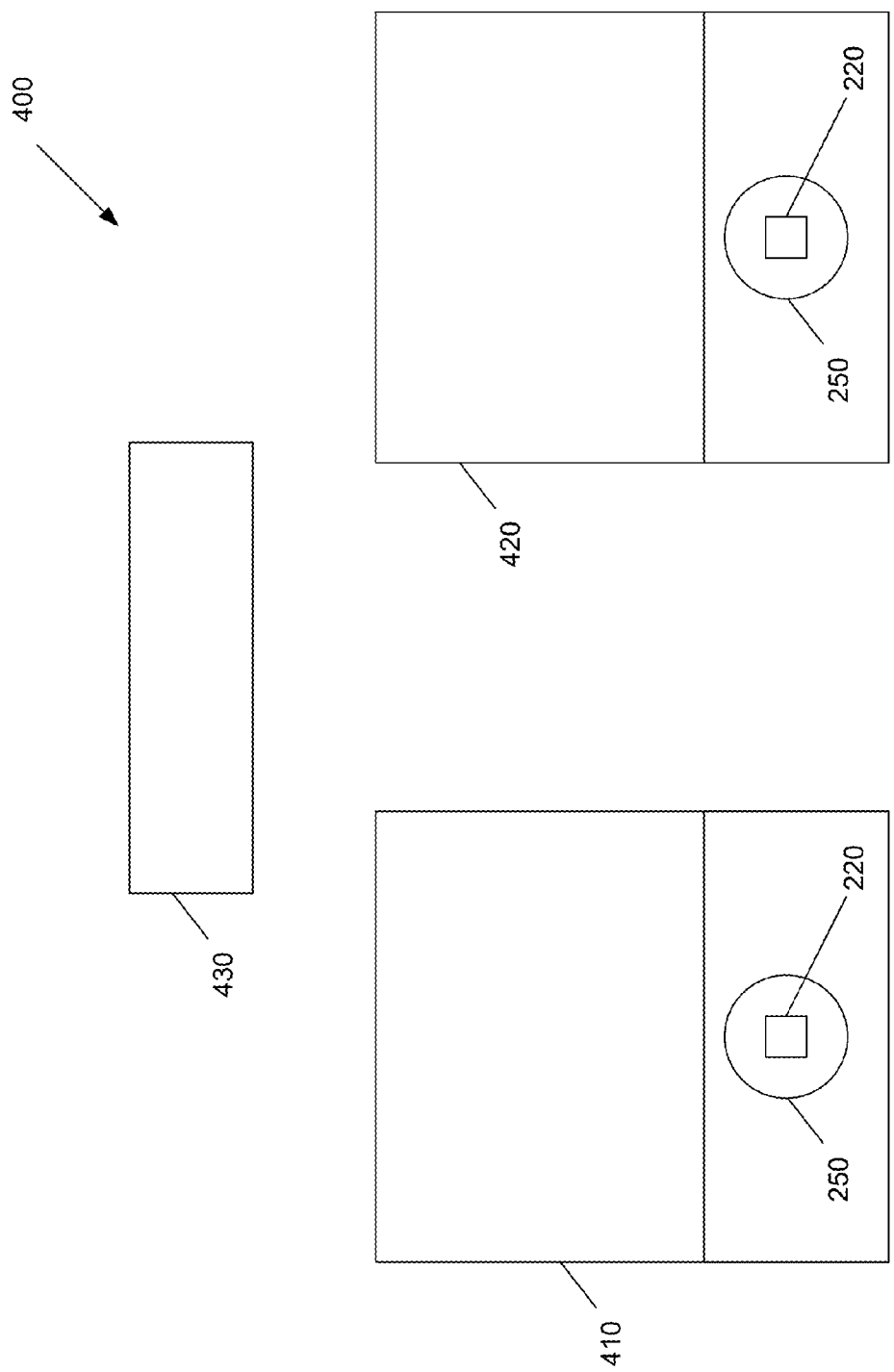
FIG. 5 shows another example system including multiple devices for estimating urine output.

For example, referring now to FIG. 5, a system 400 is shown with "dueling" urinals 410, 420. Each of the urinals 410, 420 is equipped to estimate an amount of urine output for individuals using the urinals 410, 420. A read-out 430 displays totals.

For example, two individuals can use urinals 410, 420 in a direct competition. For example, the system 400 can be programmed to estimate which individual generates a certain quantity (e.g., 12 ounces) of urine output in the least amount of time. The progress and winner can be displayed on the read-out 430.

In other examples, the system can be configured to output results over a network to a centralized server. This can allow, for example, for competitions between groups located at different places. For example, different bars can compete against one another.

Various methods can be used to display the progress on the read-out 430. For example, in one embodiment, LED lights of various colors are used, such as red, yellow, and green, to indicate an individual's progress toward a goal. In another example, a race track is formed with representations of horses for each individual. The horses move around the track based on the urine output from each individual. The individual with either the greatest quantity in a given timeframe can move the individual's horse around the track the quickest to win the competition. Other configurations are possible.

In the example shown in FIG. 5, the read-out 430 can reset upon flushing of the urinals 410, 420. A "best score" list can be maintained, and users can enter names or initials via an input device such as a keypad or touch screen (not shown). The information can be sent between the flow mechanisms 220, read-out 430, and any input devices using wired or wireless technologies (e.g., Bluetooth, WiFi, etc.). Other configurations are possible.

Figure 6:
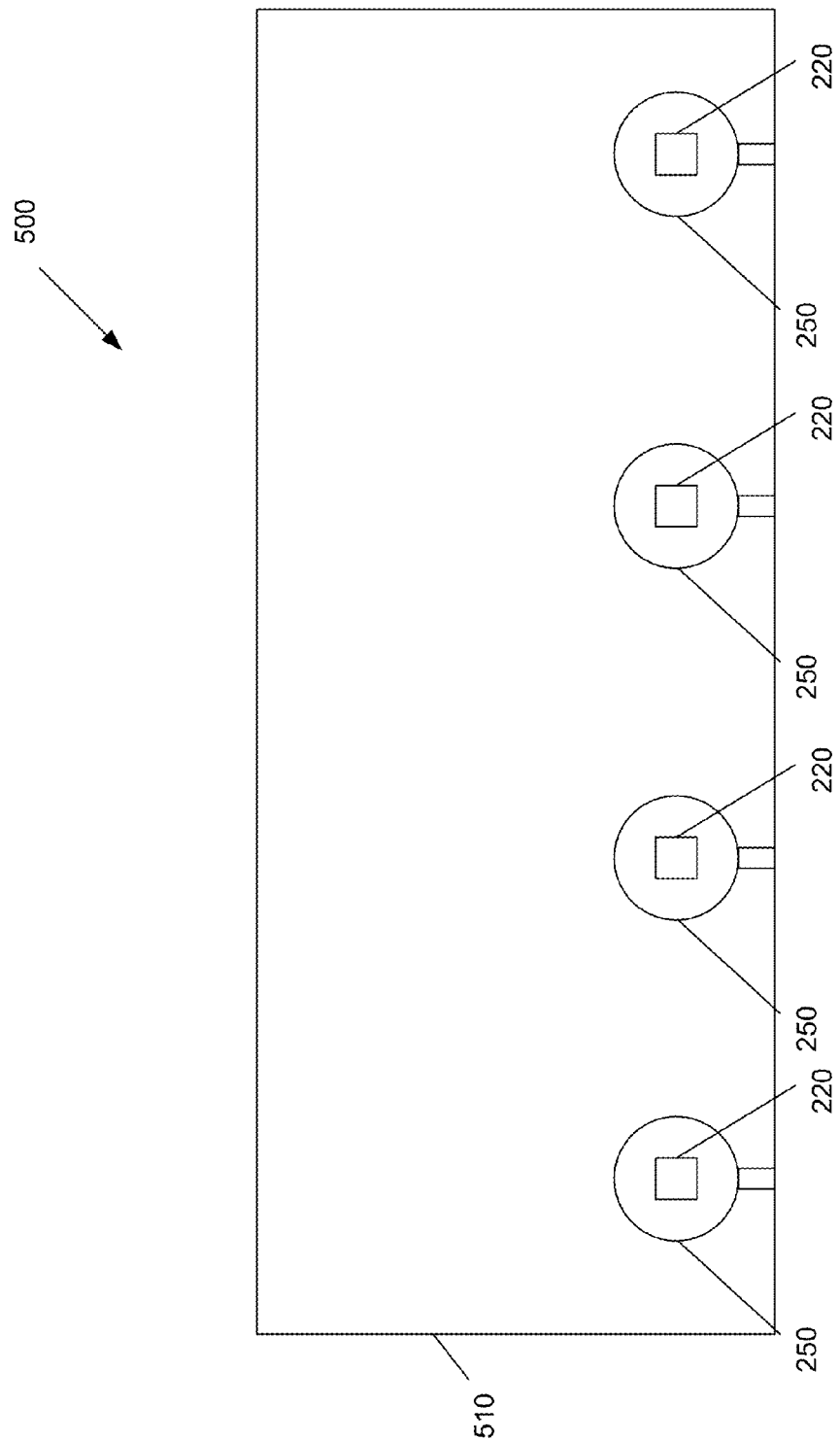
FIG. 6 shows another example system including multiple devices for estimating urine output.

Referring now to FIG. 6, another example system 500 is shown. The system 500 includes a trough style urinal 510 with a plurality of flow mechanisms 220 installed therein. Multiple individuals can use the urinal 510 at any given time to compete individually or against one another.

Various configurations can be used to form the flow mechanisms 220, as described below.

Figure 7:
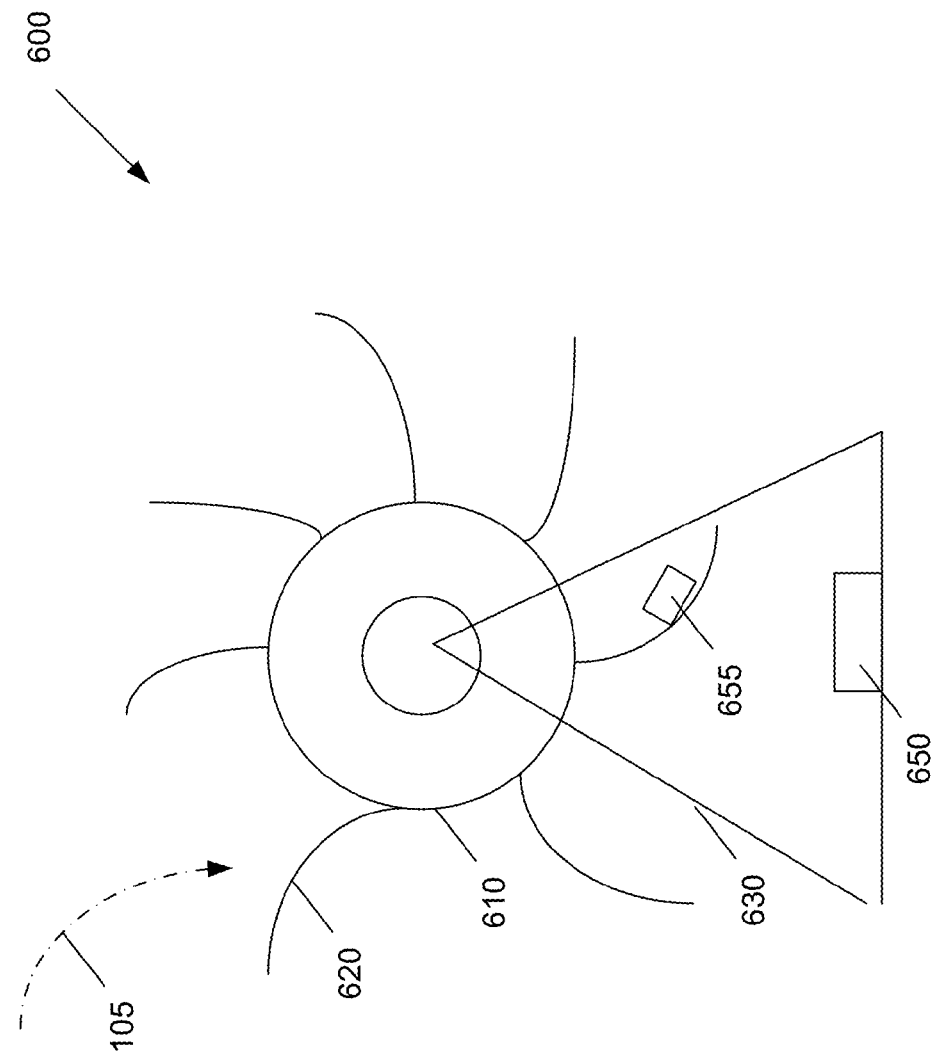
FIG. 7 shows an example flow mechanism for estimating urine output.

For example, in one embodiment shown in FIG. 7, a flow mechanism 600 includes a turbine 610 with vanes 620. The turbine 610 is mounted to a base 630 and spins when the urine stream contacts the vanes 620. As the turbine 610 spins, a magnet 655 mounted to one or more of the vanes 620 comes into close proximity with a sensor 650 (e.g., a Hall effect sensor). In this manner, the sensor 650 can calculate a total number of revolutions of the turbine 610 over a given time. This can be used to estimate urine output. The turbine 610 can be placed behind a guard to protect the turbine 610, and the base 630 can be coupled to the urinal. For example, the base 630 could be cast into the porcelain of the urinal or otherwise attached thereto.

Figure 8:
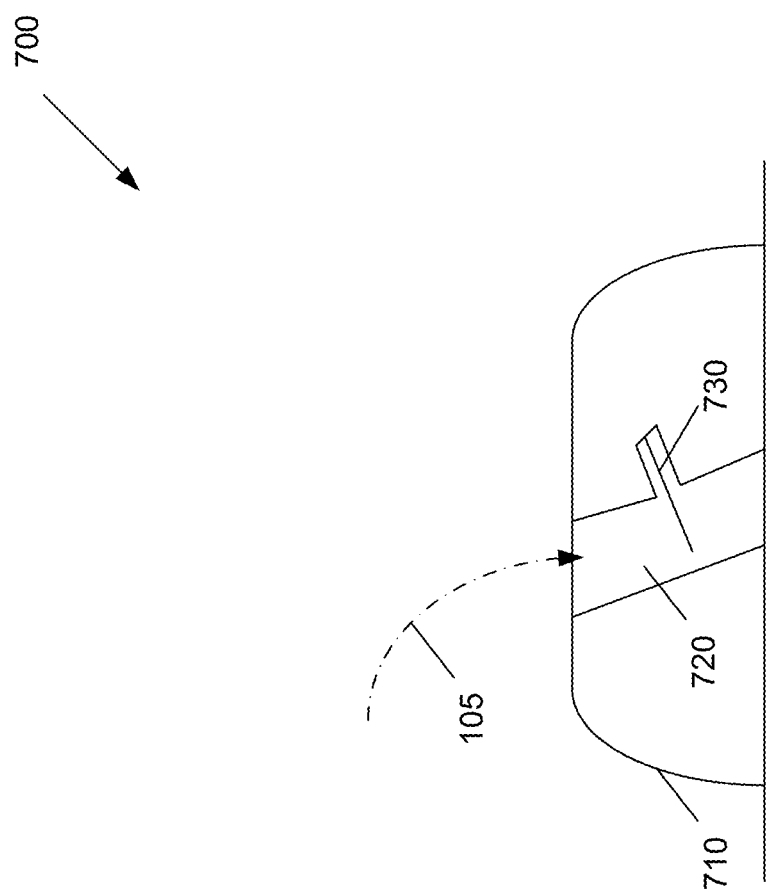
FIG. 8 shows another example flow mechanism for estimating urine output.

In FIG. 8, an example flow mechanism 700 includes a strain gauge apparatus 710. The strain gauge apparatus 710 includes a flow channel 720 through which the urine stream 105 is directed. A strain gauge 730 is positioned to extend into the flow channel 720. As the urine stream flows through the channel 720, the strain gauge 730 is deflected. By measuring the amount of deflection over time, an estimate of the urine output can be calculated. In examples, the strain gauge apparatus 710 can be powered by batteries or hard wired.

For example, the strain gauge 730 can measure the amount of deflection at a given point in time. The flow mechanism 700 can be configured to estimate a particular flow rate at a given deflection. By measuring the deflection over time and estimating a flow rate at each measured deflection, a total estimate of the urine output can be calculated.

Figure 9:
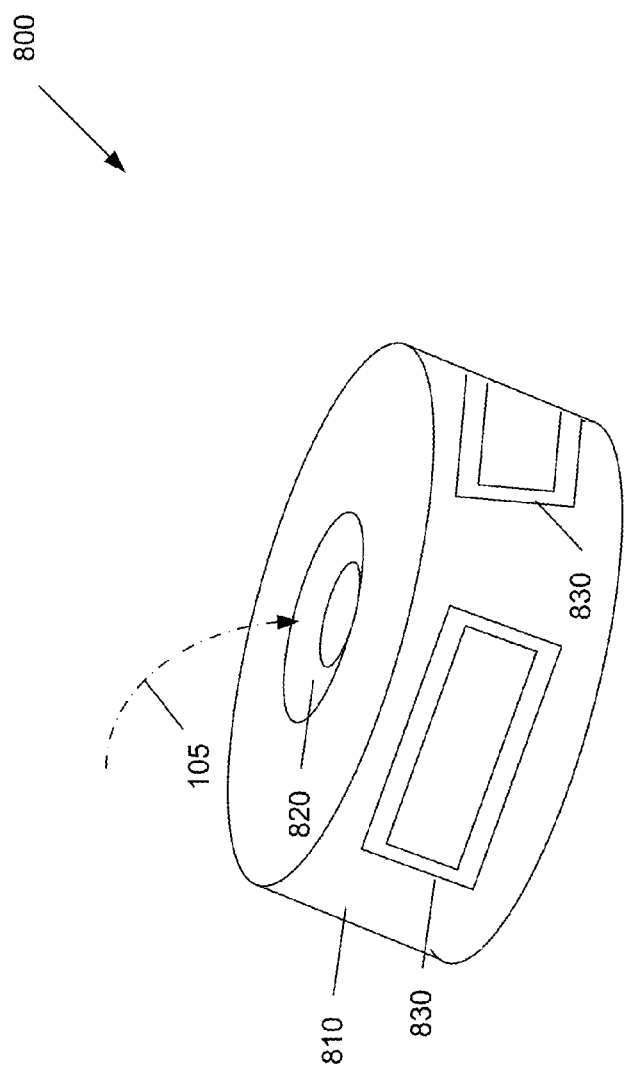
FIG. 9 shows another example flow mechanism for estimating urine output.
Figure 10:
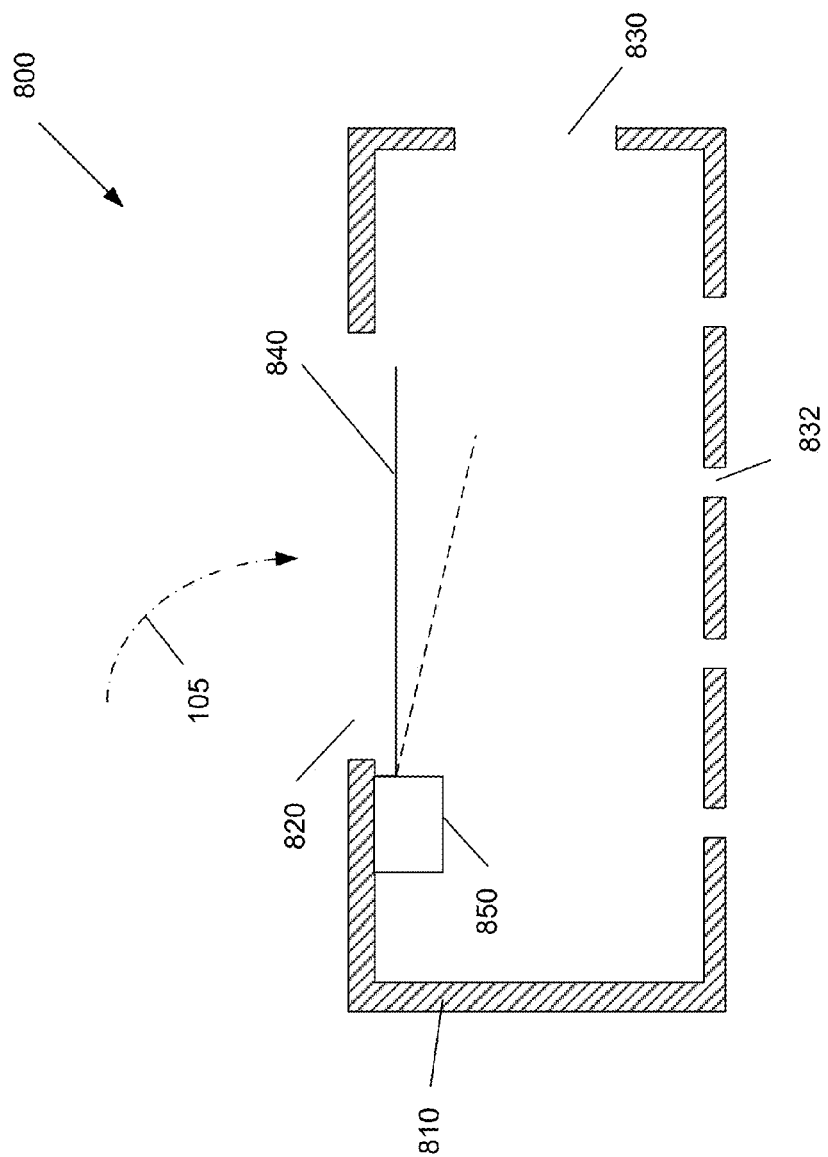
FIG. 10 shows a cross-sectional view of the flow mechanism of FIG. 9.

Referring now to FIGS. 9 and 10, another strain gauge apparatus 800 is shown. The strain gauge apparatus 800 is configured in the shape of a typical "puck" 810 that is placed in a urinal. The puck 810 includes an aperture 820 formed in a top of the puck 810 and a hollow interior. One or more openings 830, 832 are also formed on the sides and/or bottom of the puck 810.

When the urine stream 108 is directed into the aperture 820, the urine contacts a strain gauge 840. This deflects the strain gauge 840 (see dashed line). The deflection is measured over time to estimate urine output. A module 850 can be connected to the strain gauge 840 to estimate time of deflection and/or amount of deflection. The module 850 can be configured to wirelessly transmit the information for display to the individual.

In yet another example shown in FIG. 1, one or more sensors are used. The sensors project a beam between the sensors, such as an infra red beam. The beam is distorted or broken with the urine stream 105 passes between the sensors. By measuring a duration of the disruption of the beam, an estimate of the urine output can be calculated. In some examples, the amount of disruption can be measured to provide a better estimate of the amount of urine in the urine stream, or even a speed of the urine stream.

Other configurations are possible. For example, a motion sensor can be used to estimate the urine stream. In another embodiment, the flow mechanism is configured to collect the urine output and physically measure the urine through weight or volume measurements before discarding the urine.

In some embodiments, the systems are configured to minimize a back-splash of the urine stream as the urine stream enters the systems. For example, if placed in a urinal, the system can be optimized to minimize an amount of urine that splashes out of the system. In some examples, a target is provided to direct the user to aim at a particular spot so that splashing of the urine stream is minimized.

In alternative embodiments, the systems described herein can be used for other purposes as well. For example, the systems can be used to monitor the amount of urine produced by individuals over a period of time. If the establishment is a bar, the bar can use this information to estimate an intoxication level of the individual. Using this information, the bar can, for example, estimate when a patron is too intoxicated to drive and suggest alternative transportation. In another example, the individual or individuals with the highest outputs or scores can win a free ride home from the establishment.

In another embodiment, the systems can be used to assist in training children to use the toilet. The systems can make the process fun for a child, thereby increasing the chances that the child will use the toilet.

Figure 11:
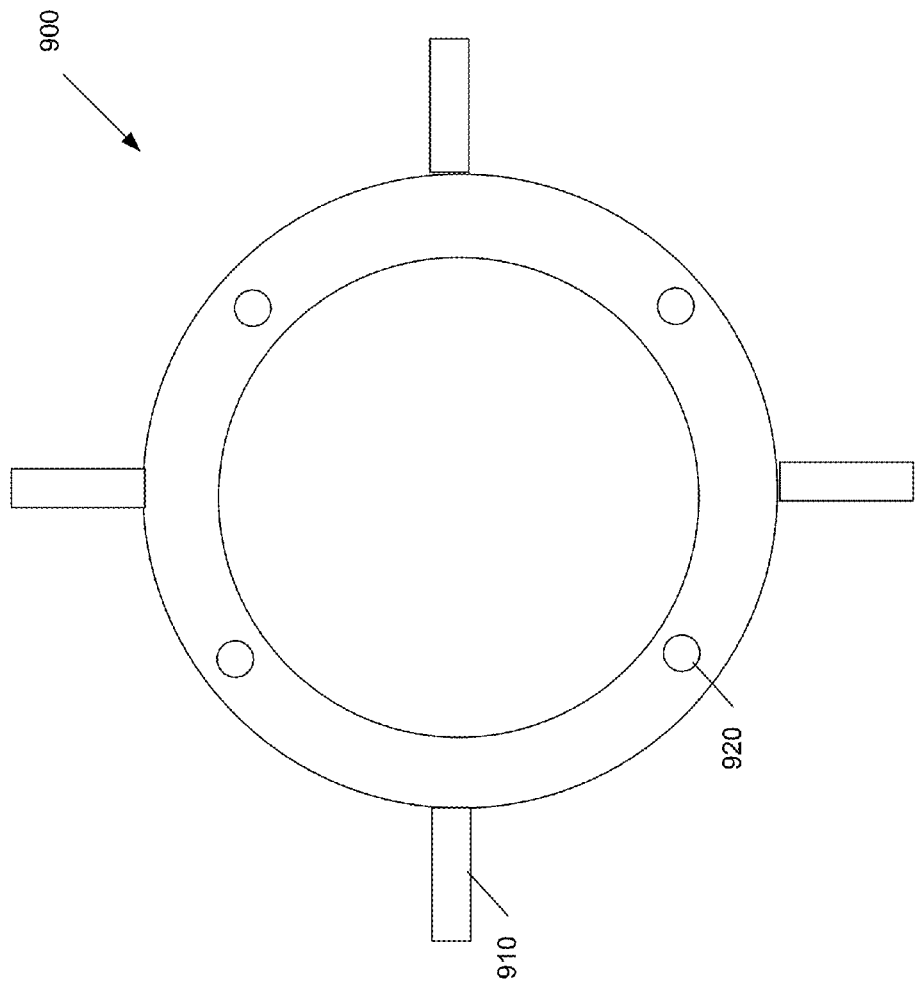
FIG. 11 shows another example flow mechanism for estimating urine output.

For example, a form of strain gauge apparatus 900 is shown in FIG. 11. The stain gauge 900 can be employed in a household toilet with a simple ring of identical or different LED lights 920 that illuminate in order based on flow rate or duration. The strain gauge apparatus 900 can be suspended over the toilet aperture through supports 910 on either side attached on a proximal end to the strain gauge apparatus 900 and to the distal end to the toilet walls or to one toilet wall. The strain gauge apparatus 900 is ideally removable from the toilet for easy cleaning and battery replacement.

In another example, the systems can be used to track water loss for an individual. For example, athletes or other individuals may need to, or simply want to monitor an amount of water loss to avoid dehydration. Such dehydration may present serious health risks during high performance athletic competitions, such as marathons or triathlons. Alternatively, because proper hydration is a general aim of healthful daily living, even non-athletic individuals may use the systems described herein to maintain hydration. The systems described herein can be used to estimate the amount of water lost through urination.

As with the household version of the strain gauge apparatus 900, an adult version used for physical health purposes may have an LCD display with a score representing estimated water loss or estimated water replacement need. This version of the device may be portable for use during travel or at competitive sports events. Medical care providers could use this adult version of the device with patients experiencing below or above-normal daily fluid loss. In the former instance, a low total daily score could indicate dehydration or some other physical problem resulting in low urine production (oliguria), such as a urinary tract obstruction, renal failure, or hypovolemic shock. In the latter instance, a very high total daily score could indicate diabetes or other medical condition resulting in polyuria.

Figure 12:
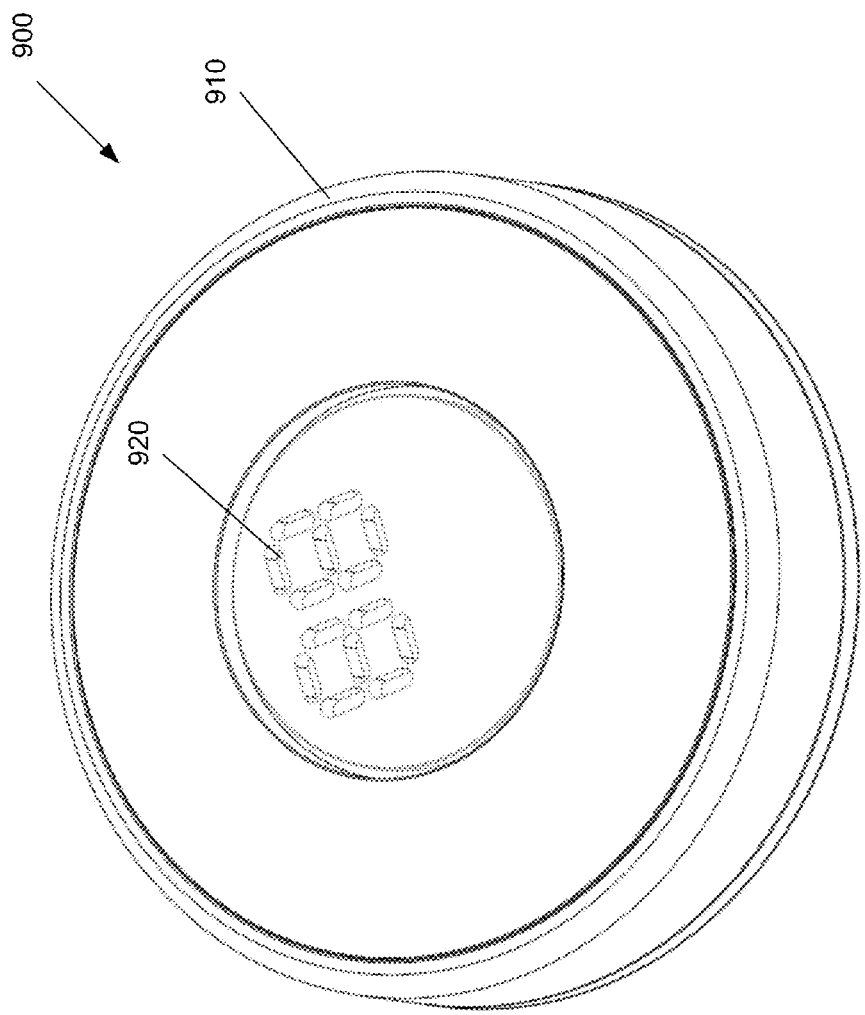
FIG. 12 shows another example flow mechanism for estimating urine output.
Figure 13:
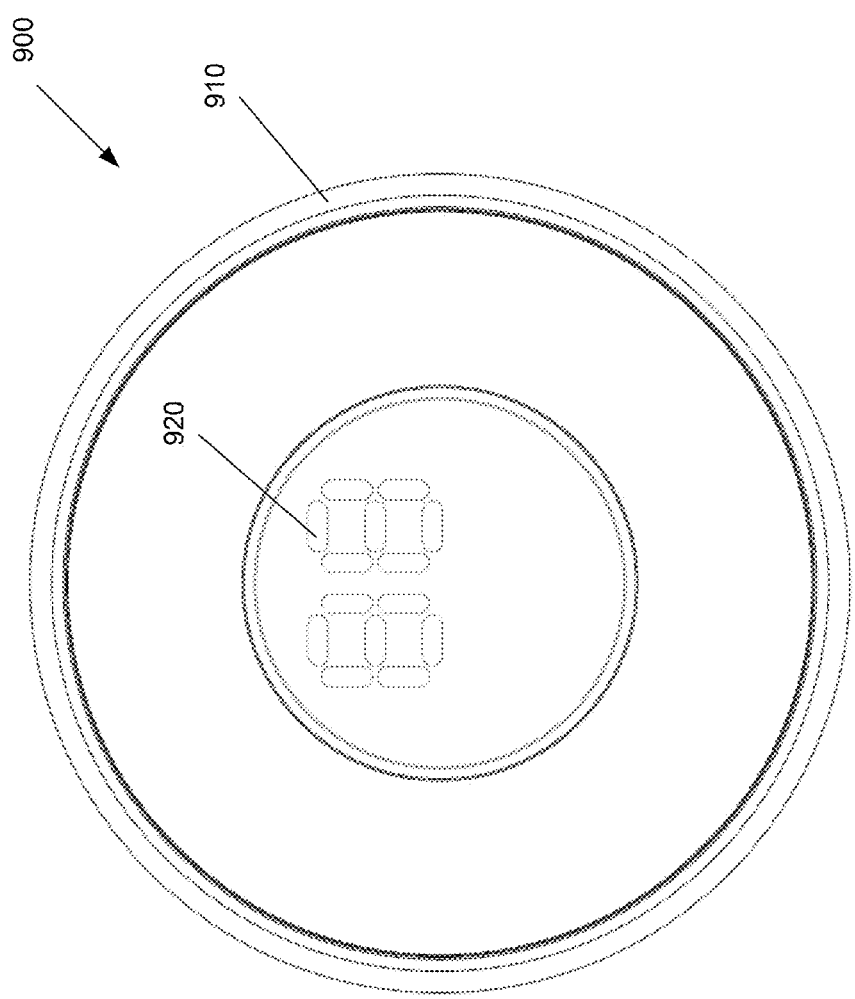
FIG. 13 is a top view of the flow mechanism of FIG. 12.

Referring now to FIGS. 12-14, another example flow mechanism 900 is shown. This flow mechanism includes a main body 910 and a display 920. Generally, the flow mechanism 900 is configured as a sealed, water tight container, so that fluid cannot enter the main body 910. The display 920 can display certain information to the user, as described further below.

Referring specifically to FIG. 14, the flow mechanism 900 includes various components located within the main body 910. Generally, the main body 910 includes an upper housing 942 and a lower housing 944. The upper and lower housing 942, 944 are connected using, for example, bolts or other fasteners. The upper and lower housing 942, 944 are made of a polycarbonate. Other durable materials, such as other plastics or metal, can be used for the housing.

Various components are positioned within the upper and lower housings 942, 944. For example, a lens 932 is positioned over a cover 934. The lens 932 is at least semi-transparent so that a user can see the display 920 mounted in the cover 934. In this example, the lens 932 and the cover 934 are made of a polycarbonate.

Underneath the cover 934 is an elastomeric ring 936. The ring 936 is made of a soft rubber of any lower durometer, and the ring is fastened to the upper housing 942 using, for example, glue. The lens 932 and the cover 934 are, in turn, connected to the ring 936 using, for example, glue. The ring 936 is compressible, as noted below.

An accelerometer is mounted to a board 938 located under the ring 936. The accelerometer is positioned so that the accelerometer can measure small changes in pressure applied to the lens 932. Specifically, when pressure is applied to the lens 932, such as when a urine stream is directed thereto, the lens 932 is forced downward and compresses the ring 936. The accelerometer measures this change.

In this example, the accelerometer is a 3-axis low power accelerometer made by Freescale Semiconductor, part MMA7331. Other accelerometers can be used as well. The accelerometer is soldered to the board 938, and is designed to be oriented with its face substantially parallel to the cover 934. This embodiment measures acceleration in that axis (i.e., the accelerometer's z-axis, perpendicular to the surface of the cover 934).

A power source 940, such as batteries, is mounted within the upper housing 942 as well. The power source 940 can be used to power the accelerometer and the display 920.

In this example, the flow mechanism 900 is sized to fit into a standard toilet or urinal. For example, the flow mechanism 900 is, in this example, approximately 3.5 inches in diameter and 1 inch tall. Other configurations are possible.

In one example use, the flow mechanism 900 is mounted in a urinal basin or toilet, whether by way of a support bracket or adhesive attachment. In some embodiments, the flow mechanism can simply be set down or leaned against a urinal structure.

The flow mechanism 900 stays in a low-power setting waiting for disturbance of the accelerometer behind the display 920. As noted, the ring 936 allows for the accelerometer to perceive motion of the cover 932 upon a stream of urine being directed thereon.

Motion on the flow mechanism 900 wakes the flow mechanism 900 up, and the flow mechanism 900 begins counting, such as from 0-99. The duration of the count continues as long as disturbance continues until either (a) the counter hits a preset number, such as 99, (b) the urine flow stops to the preset number (e.g., could be 2-10 seconds with no disturbance on the unit), or (c) an agreed time-out is reached (e.g., the user gets 30 seconds only to hit the target to reach the preset number or the flow mechanism 900 times out and gives the user a final score—the highest number the user was able to reach).

The time variations can be adjusted in software based on desired user features. For example, the unit could be set to only cease counting when the user hits 99 or is no longer able to agitate the target (they get to keep "shooting" as long as they are able to). The flow mechanism 900 could also include a delay period following a score to account for flushing (to avoid unintended game play and battery usage).

The display 920 could also include other features, such as a ring of lights that goes around in a circle, with speed increasing based on intensity.

The flow mechanism 900 is designed to allow for external agitation, but keeps all parts waterproof. Ideally, little or no fluid goes through the flow mechanism 900. There are not moving parts except for slight motion of the accelerometer.

The various embodiments described above are provided by way of illustration only and should not be construed to limiting. Various modifications and changes that may be made to the embodiments described above without departing from the true spirit and scope of the disclosure.

What is claimed is:

1. A device for estimating a stream of urine, the device comprising:
   a sealed, watertight container;
   a measuring unit configured to measure a characteristic of the stream of urine, wherein the measuring unit is an accelerometer and is positioned within the container;
   a power source positioned within the container; and
   an indicator to provide an indication of the characteristic of the stream of urine;
   wherein the device remains in a lower-power setting when not in use; and
   wherein the device wakes and measures a duration of the stream of urine when the accelerometer senses the stream.

2. The device of claim 1 wherein the device further comprises a compressible portion positioned within the container.

3. The device of claim 2 wherein the compressible portion is a ring.

4. The device of claim 1 wherein the characteristic of the stream of urine sensed by the accelerometer is the pressure of the stream.

5. The device of claim 1 wherein the characteristic of the stream of urine sensed by the accelerometer is the amount of the stream.

6. The device of claim 1 wherein the indicator comprises a numerical display.

7. The device of claim 1 wherein the indicator comprises one or more lights.

8. A device for sensing a stream of urine, the device comprising:
- a container that provides a watertight environment within the container;
- a measuring unit comprising an accelerometer, the measuring unit sensing the stream of urine;
- a power source positioned within the container;
- a display to provide an indication of a characteristic of the stream of urine sensed by the measuring unit.

9. The device of claim 8 wherein the characteristic of the stream of urine sensed by the measuring unit is the duration of the stream.

10. The device of claim 8 wherein the characteristic of the stream of urine sensed by the measuring unit is the pressure of the stream.

11. The device of claim 8 wherein the characteristic of the stream of urine sensed by the measuring unit is amount of the stream.

12. The device of claim 8 wherein the display comprises a numerical display.

13. The device of claim 8 wherein the display comprises one or more lights.

* * * * *